United States Patent [19]

Schurgin

[11] 4,093,291
[45] June 6, 1978

[54] CONTACT LENS APPLICATION AND REMOVAL INSTRUMENT

[76] Inventor: Herbert L. Schurgin, 26 Juniper St., Wenham, Mass. 01984

[21] Appl. No.: 825,184

[22] Filed: Aug. 17, 1977

[51] Int. Cl.² ............................................. A61F 9/00
[52] U.S. Cl. .................................................. 294/1 CA
[58] Field of Search ................. 294/1 CA, 33, 64 R, 294/99 R; 81/43; 128/303 R, 321, 354; 351/160

[56] References Cited

U.S. PATENT DOCUMENTS

| | | | |
|---|---|---|---|
| 3,139,298 | 6/1964 | Grabiel | 294/1 CA |
| 3,304,113 | 2/1967 | Hutchison | 294/1 CA X |
| 3,600,028 | 8/1971 | Henning | 294/1 CA |
| 3,743,337 | 7/1973 | Crary | 294/1 CA |

FOREIGN PATENT DOCUMENTS 1,395,355  3/1965  France .............................. 294/1 CA

*Primary Examiner*—Johnny D. Cherry
*Attorney, Agent, or Firm*—Weingarten, Maxham & Schurgin

[57] ABSTRACT

An instrument for applying a contact lens to a user's eye and for removing a contact lens therefrom. The instrument is especially adapted for use with soft contact lenses and comprises a central footplate having a curved surface on which a lens can be retained by liquid adhesion and having an illuminated aperture providing an accurate and easily visible target for alignment of the instrument with the eye, and a pair of resilient arms between which the footplate is disposed and having shaped end portions for engagement of a contact lens. The arms are movable toward each other to grasp the edges of a contact lens worn by the user for removal of the lens from the cornea onto the footplate.

11 Claims, 8 Drawing Figures

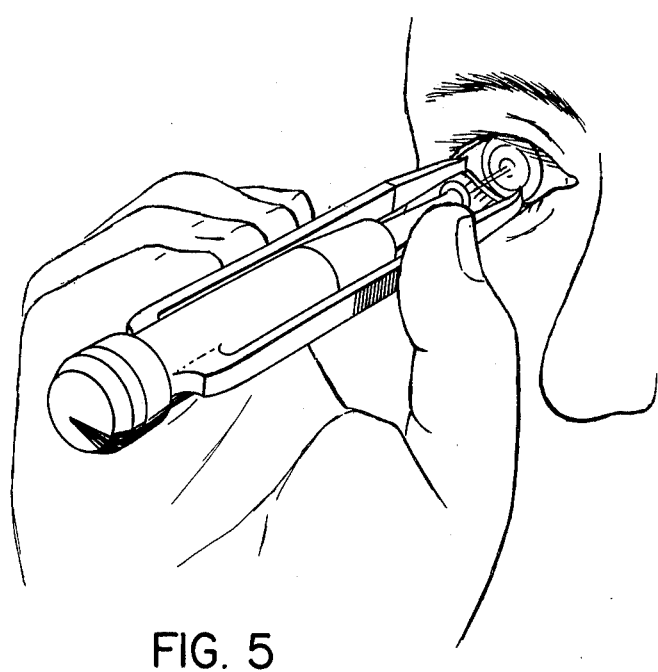
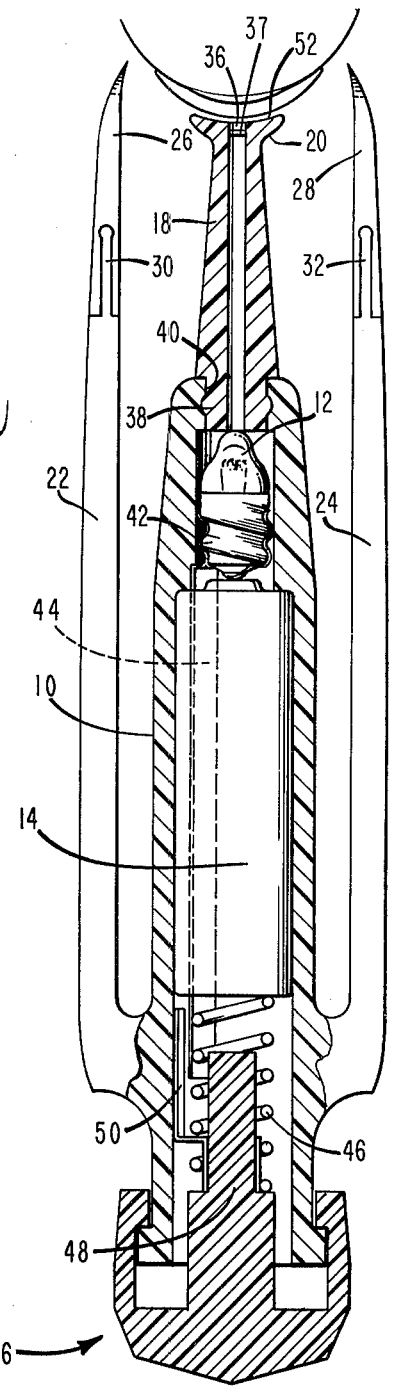
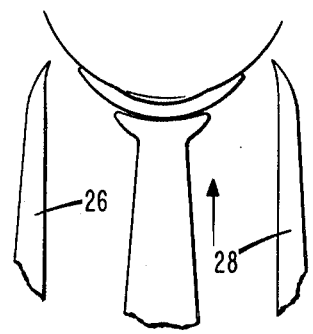
FIG. 2
FIG. 3
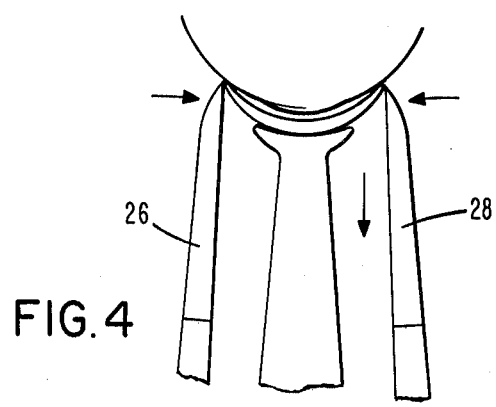
FIG. 4

CONTACT LENS APPLICATION AND REMOVAL INSTRUMENT

FIELD OF THE INVENTION

This invention relates to instruments for application and removal of contact lenses and more particularly for use with soft contact lenses.

BACKGROUND OF THE INVENTION

Contact lenses are usually applied to the eye and removed therefrom manually by the user. For application of a contact lens, the lens is placed concave side upward on a finger of the user and placed onto the cornea. For removal of the lens from the eye, the user grasps the lens at its edges using his thumb and forefinger to lift the lens off of the cornea. In the case of a soft contact lens, the user manually buckles the lens by pinching the grasped edges to lift the lens off the cornea. Many persons, however, experience considerable difficulty in placing and removing contact lenses, especially persons having limited manual dexterity and post-operative cataract patients who have minimal vision in the absence of the crystalline lens of the eye.

Devices have been proposed heretofore for application and removal of contact lenses, in general for use with hard contact lenses. None of the prior art devices has yet been wholly satisfactory, either with respect to facility of use or effectiveness of performance. This is especially so with respect to soft contact lenses which are subject to tearing or other damage. One known type of applicator employs a support on which a lens is placed and including means for aligning the lens with the user's eye prior to application of the lens. One such applicator is shown in U.S. Pat. No. 3,139,298 wherein the lens support is a cylindrical sleeve having a curved outer edge for placement of a lens, and having within the sleeve an illuminated bullseye target by which a user aligns the lens for placement onto the cornea. Another applicator employing an illuminated target is shown in U.S. Pat. No. 3,743,337 and includes an annular lens support provided at the opening of a translucent bottle containing an opthalmic liquid and which is supported on a handle containing a battery powered light source. The lens is retained on the support by surface tension of the liquid within the bottle.

Another known type of applicator is shown in U.S. Pat. Nos. 2,379,629 and 3,091,328 and which employs a suction cup for retaining a lens on a support for application to the eye or by which the lens is removed by suction from the eye. A further suction type removal device is shown in U.S. Pat. No. 2,919,696 and which also includes an applicator having an eye cup which engages the eyelid to retract the skin around the eye to facilitate lens application. Yet another lens applicator, shown in U.S. Pat. No. 3,031,918, includes a lens support ring carried on a frame which also includes a target for visual alignment during application. An applicator comprising a lens support ring adapted to be inserted on the finger of a user is shown in U.S. Pat. No. 3,132,887.

SUMMARY OF THE INVENTION

Briefly, the present invention provides a simple and easily usable instrument for applying a soft contact lens to the user's eye and for removing a soft contact lens therefrom without discomfort to the user or damage to the lens. The novel instrument comprises a central footplate having a curved surface on which a soft contact lens can be retained by liquid adhesion and having an illuminated aperture in the curved surface which provides an accurate and easily visible target for alignment of the lens and instrument with the eye, and a pair of resilient arms between which the footplate is disposed, the arms being movable toward and away from the footplate and having shaped end portions for engagement of the edges of a soft contact lens. The arms are operative to be manually moved toward each other to grasp the confronting opposite edges of a soft contact lens worn by the user, causing the lens to outwardly buckle into engagement with the footplate, the lens being retained by the footplate due to liquid adhesion.

DESCRIPTION OF THE DRAWINGS

The invention will be more fully understood from the following detailed description taken in conjunction with the accompanying drawings, in which:

FIG. 1 is a side view, partly in section, of a contact lens application and removal instrument embodying the invention;

FIG. 2 is a cutaway side view of a portion of the embodiment of FIG. 1 illustrating support of a contact lens on the footplate;

FIG. 3 is a cutaway side view of a portion of the embodiment of FIG. 1 illustrating placement of a contact lens onto the cornea;

FIG. 4 is a cutaway side view of a portion of the embodiment of FIG. 1 illustrating use of the instrument in lens removal from the cornea;

FIG. 5 is a pictorial view illustrating use of the instrument in alignment with a user's eye;

DETAILED DESCRIPTION OF THE INVENTION

Figure 7:
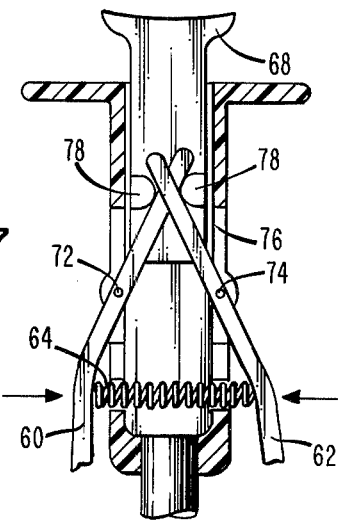
FIG. 7 is a cutaway sectional view of a plunger mechanism useful in the embodiment of FIG. 6.

Referring to FIG. 1, the novel instrument for applying and removing a soft contact lens is shown and includes a generally tubular body or housing 10 having a chamber containing a light-bulb 12 or other light emitting element and a battery 14, a cap assembly 16 at the rearward end of body 10 and, at the forward end thereof, an outwardly extending member 18 which terminates in a footplate 20. First and second resilient arms 22 and 24 are oppositely disposed with respect to body 10, the arms terminating in respective removable end portions 26 and 28, which extend along the longitudinal axis of body 10 beyond footplate 20 by a predetermined amount. The body 10 and the arms 22 and 24 are preferably formed as an integral unit such as by molding of a suitable plastic material. The end portions 26 and 28 of respective arms 22 and 24 are retained on the arms by any suitable means such as fingers 30 and 32 provided on the respective ends of arms 22 and 24 and cooperative with slots in end portions 26 and 28. An opening 34 is provided through member 18 terminating in an aperture 36 in the footplate surface and through which light from bulb 12 can be transmitted for emission from the aperture. The member 18 is removably retained in the end of housing 10 such as by means of plug portion 38 which is insertable and retained by cooperative opening 40 in body 10. The aperture 36 is sealed such as by a light transmissive plug 37 just rearward of the aperture to prevent entrance of opthalmic liquid into the interior of body 10 thereby to avoid corrosion or contamination.

In the illustrated embodiment the bulb 12 is threaded into a socket 42 disposed within the central chamber of body 10 and which is electrically connected via a conductive strip 44 extending along the length of the body chamber to the rearward end thereof. The battery 14 is retained within the body chamber with one battery terminal in contact with the central terminal of bulb 12 and with the other battery terminal in contact with spring 46 which is retained by the central stem 48 of cap 16. A conductive strip 50 is in contact with spring 46, and upon rotation of cap 16, contacts strip 44 to complete the electrical circuit and cause illumination of bulb 12. The cap 16 serves as the on/off switch control and can also be rotated to an unlatched position for removal of the cap from the body to allow access to the body chamber for removal and replacement of the bulb and battery. Such cap assembly and electrical battery connection are themselves well-known in the art.

The member 18 is formed of surgical rubber or other material having no toxic or other adverse effect on the human eye or the contact lens and is removable from body 10 for cleaning or replacement. The footplate 20 includes a generally spherical outer surface 52 preferably having a radius of curvature slightly larger than the confronting radius of curvature of the contact lens, for reasons to be explained. The footplate is preferably resilient to yield upon slight pressure to prevent damage or discomfort to the eye. The end portions 26 and 28 on arms 22 and 24 are also formed of surgical rubber or other material compatible with safe contact of the human eye and the contact lens. The tips of end portions 26 and 28 are configured to facilitate grasping of the soft contact lens disposed on the cornea.

Figure 6:
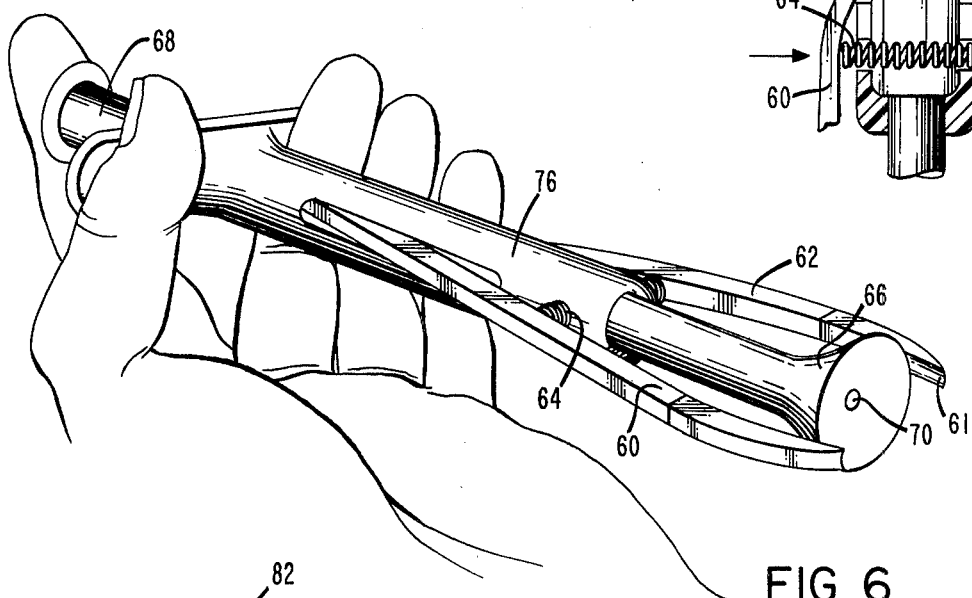
FIG. 6 is a pictorial view of an alternative embodiment of the invention.
Figure 8:
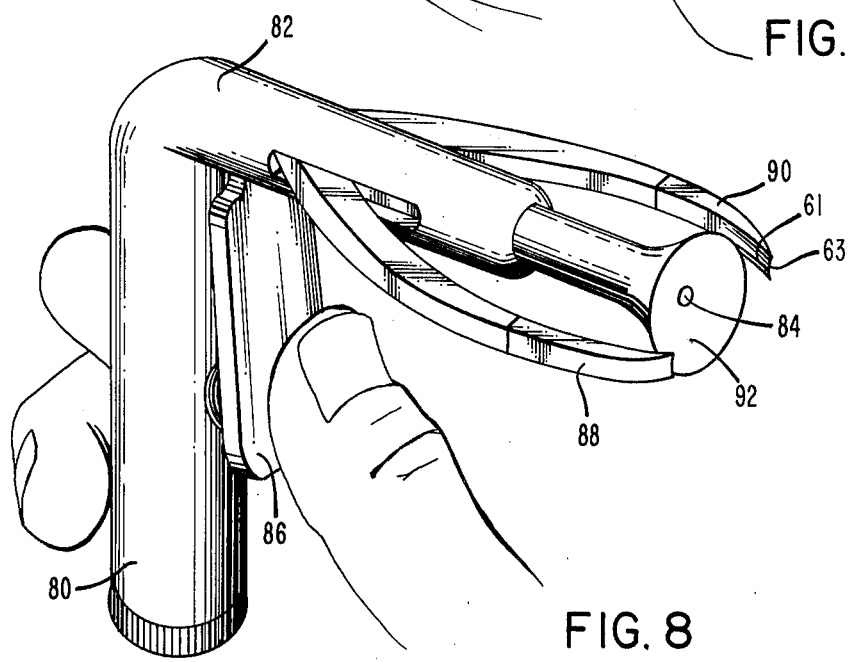
FIG. 8 is a pictorial view of a further embodiment of the invention.

In one preferred configuration, best seen in FIGS. 5 and 6, each tip is curved along a radius 61 approximating that of an associated contact lens, and is feathered to a thin flexible edge which may be adapted to slide between the contact lens and the confronting eye surface. Another tip configuration is shown in FIG. 8 and includes in addition to that of FIGS. 5 and 6, a surface 63 in a plane transverse to the plane of curve 61 and conforming to the curved surface of the sclera of the eye in order to closely engage the sclera during lens removal. It will be appreciated that the end portions of the arms can be implemented and affixed to the arms in many different ways. For example, the end portions can be sleeves having appropriately shaped tips and slidably attachable to the movable arms. Similarly, the footplate can be variously provided either integral with or attachable to member 18. The member 18 may also be part of body 10, with the footplate 20 removable from the outer end of the extended body.

For application of a lens to the eye, the lens is placed on footplate 20, as shown in FIG. 2, and is retained thereon by surface tension of the opthalmic fluid with which the lens and footplate is wetted. The user aligns the lens with the cornea by viewing the pencil beam of light transmitted through the lens via aperture 36, and the instrument is moved toward the eye until placement of the lens onto the cornea, as shown in FIG. 3. The instrument is then moved away from the eye leaving the lens in place. The lens remains on the eye upon removal of the instrument by reason of the greater adhesion of the lens on the eyeball in relation to the adhesion of the lens on the smaller area footplate. The radius of the footplate is greater than the normal radius of the cornea to minimize the contact area of the lens on the footplate. The footplate is configured to provide sufficient adhesion for support of the lens while being placed onto the eye while not materially detracting from removal of the instrument from the contact lens after placement of the lens on the cornea. During lens application, the end portions 26 and 28 of arms 22 and 24 are in their open position, spaced outward from footplate 20 by a sufficient amount to not interfere with placement of the lens onto the cornea, as seen in FIG. 3.

For removal of a soft contact lens from the cornea, the instrument is aligned by the user with his eye, as depicted in FIG. 5, by visually sighting the pencil beam emitted from aperture 36. The footplate 20 is then brought into engagement with the contact lens on the cornea. The arms 22 and 24 are manually pressed toward each other to bring the tips of end portions 26 and 28 into engagement with the confronting edges of the contact lens. The lens is buckled or vaulted by the squeezing force of the tips and is caused to move into engagement with the confronting surface of footplate 20, as shown in FIG. 4. The lens adheres to the footplate by the surface tension of the wetted contact lens and footplate surfaces, and the instrument containing the lens is withdrawn from the eye. The arms 22 and 24 can be released once the lens is seated on the footplate since the lens will remain thereon by liquid adhesion.

An alternative embodiment of the invention is shown in FIG. 6 wherein the arms are operated by a plunger mechanism. In this latter embodiment, the arms 60 and 62 are normally biased by a spring 64 into a closed position, with the tips of the arms slightly forward of the periphery of footplate 66. The end portions of the arms 60 and 62 are removable as described above. Upon depression of plunger 68, the arms are caused to move outward. For lens removal employing the embodiment of FIG. 6, the instrument handle is grasped by the user and plunger 68 depressed to move arms 60 and 62 outward. The instrument is then moved toward the eye with the aid of the aligning pencil of light emanating from the aperture 70 of footplate 66 until the footplate engages the contact lens on the cornea. The plunger 68 is then released causing arms 60 and 62 to be moved inward by action of spring 64, engaging the edges of the contact lens and buckling the lens into engagement with the footplate, at which time the lens is withdrawn from the eye by movement of the instrument away from the eye. The mechanism for operation of the arms can be of any well-known implementation. As an example, shown in FIG. 7, the arms 60 and 62 are pivoted about respective pins 72 and 74 on handle 76, the upper ends of the arms being engaged by tabs 78 of plunger 68. Depression of the plunger causes outward movement of the arms, while release of the plunger causes inward movement of the arms by action of spring 64.

A further embodiment is shown in FIG. 8 wherein the instrument body is of right angle configuration, the handle portion 80 containing a battery and an operating lever 86, and portion 82 containing the movable arms 88 and 90 and footplate 92. The aperture 84 in footplate 92 can be coupled to the light source disposed within the body by a light pipe such as a Lucite rod to provide conduction of light in well-known manner from the light source to the aperture. The arms are operated by lever 86 by any well-known mechanism.

It will be appreciated that the invention can include various modifications and alternative implementations without departing from the spirit and true scope thereof. It will also be appreciated that the invention can be employed with hard contact lenses, although preferably for use with soft lenses. Accordingly, the invention is not to be limited by what has been particularly shown and described except as indicated in the appended claims.

What is claimed is:

1. An instrument for application onto and removal of a contact lens from a user's eye comprising:
   a body adapted to be hand-held by a contact lens user and having a chamber containing an illumination source;
   first and second arms supported by said body and outwardly extending therefrom in spaced relationship to each other, said arms having end portions of a material and configuration for safe engagement with a user's eye;
   said arms being manually movable toward and away from each other;
   a footplate supported by and outwardly extending from said body between said first and second arms and having a curved outer surface for supporting a contact lens thereon, and an aperture centrally disposed in said curved surface through which light is emitted from said illumination source to provide a visual alignment target by which the instrument can be aligned with a user's eye; and
   said first and second arms having end portions extending by a predetermined amount beyond said footplate, the tips of said end portions being configured to facilitate grasping of the confronting peripheral edges of a contact lens on a user's eye.

2. The instrument of claim 1 wherein the tip of each end portion of said arms includes a curved surface having a radius approximating that of the contact lens.

3. The instrument of claim 2 wherein the tip of each end portion of said arms includes a second curved surface transverse to the first curved surface and conforming to the sclera of the user's eye.

4. The instrument of claim 1 wherein the tip of each end portion of said arms is feathered to a thin flexible edge.

5. The instrument of claim 1 wherein the end portions of said arms are removably supported on the respective arms.

6. The instrument of claim 1 wherein said footplate is removably supported on said body.

7. The instrument of claim 1 wherein said footplate has a curved outer surface of a radius greater than the radius of curvature of the contact lens to minimize the contact area between the contact lens and the footplate.

8. The instrument of claim 1 wherein said body and said arms are integrally formed as a unitary structure, and said arms being resiliently disposed in a normally open position.

9. The instrument of claim 1 wherein said illumination source includes a battery and light emitting element operatively disposed within said chamber.

10. An instrument for application onto and removal of a contact lens from a user's eye comprising:
    a body adapted to be hand-held by a user and having a chamber containing an illumination source;
    first and second arms supported on said body in spaced relationship to each other and having end portions extending longitudinally of said body;
    a footplate supported by and longitudinally extending from said body between said first and second arms and having a curved outer surface for supporting a contact lens thereon, and an aperture centrally disposed in said curved surface through which light is emitted from said illumination source to provide a visual alignment target by which the instrument can be aligned with a user's eye;
    said end portions of said first and second arms extending longitudinally of said body beyond the curved outer surface of said footplate by a predetermined distance;
    the end portions of said first and second arms each having a tip configured to grasp a contact lens worn by a user upon manual movement of said arms toward each other such that the contact lens is buckled off of the cornea into engagement with the curved surface of said footplate; and
    said end portions and said footplate being of a material suitable for safe engagement with a user's eye and with the contact lens.

11. The instrument of claim 10 including a light transmissive sealing element in the aperture of said footplate to prevent entrance of liquid into said body.

* * * * *